(12) United States Patent
O'Leary

(10) Patent No.: US 11,633,730 B2
(45) Date of Patent: Apr. 25, 2023

(54) CELL SORTER IN A SEALED SYSTEM UNDER CONTROLLED ATMOSPHERE

(71) Applicant: INDIANA UNIVERSITY RESEARCH AND TECHNOLOGY CORPORATION, Indianapolis, IN (US)

(72) Inventor: Heather O'Leary, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 236 days.

(21) Appl. No.: 16/637,949

(22) PCT Filed: Aug. 22, 2018

(86) PCT No.: PCT/US2018/047617
§ 371 (c)(1),
(2) Date: Feb. 10, 2020

(87) PCT Pub. No.: WO2019/040676
PCT Pub. Date: Feb. 28, 2019

(65) Prior Publication Data
US 2020/0206727 A1 Jul. 2, 2020

Related U.S. Application Data

(60) Provisional application No. 62/548,953, filed on Aug. 22, 2017.

(51) Int. Cl.
*B01L 1/02* (2006.01)
*B25J 21/02* (2006.01)

(52) U.S. Cl.
CPC ............. *B01L 1/02* (2013.01); *B25J 21/02* (2013.01); *B01L 2200/028* (2013.01); *B01L 2200/0652* (2013.01); *B01L 2300/046* (2013.01); *B01L 2300/1883* (2013.01)

(58) Field of Classification Search
None
See application file for complete search history.

(56) References Cited

U.S. PATENT DOCUMENTS

| | | | | |
|---|---|---|---|---|
| 5,641,457 A | * | 6/1997 | Vardanega | ................ B01L 1/04 250/461.2 |
| 5,730,777 A | * | 3/1998 | Petersen | .................. B25J 21/02 95/12 |
| 6,974,197 B1 | * | 12/2005 | Henry | ....................... B01L 1/50 73/431 |

(Continued)

OTHER PUBLICATIONS

Bair WJ. "Plutonium inhalation studies, (a series of lectures given in Japan in 1969 at the invitation of the Japanese Atomic Energy Commission)," BNWL-1221. BNWL Rep. Feb. 1970:1.1-8. (Year: 1970).*

(Continued)

*Primary Examiner* — Matthew D Krcha
(74) *Attorney, Agent, or Firm* — Barnes & Thornburg, LLP

(57) ABSTRACT

The present invention relates generally to an apparatus that is able to provide a sealed chamber system including a cell sorter, that allows for various oxygen tensions of choice to be maintained during cell harvest, sorting (and isolation of sub-populations of cells), analysis, etc.

9 Claims, 14 Drawing Sheets

(56) References Cited

U.S. PATENT DOCUMENTS

| | | | |
|---|---|---|---|
| 2011/0278997 A1* | 11/2011 | Wilkins | B25J 21/02 312/1 |
| 2015/0139855 A1 | 5/2015 | Tanimoto | |
| 2015/0192313 A1 | 7/2015 | Yokoi et al. | |
| 2016/0096171 A1 | 4/2016 | Michida | |

OTHER PUBLICATIONS

PCT International Search Report and Written Opinion completed by the ISA/US dated Oct. 1, 2018 and issued in connection with PCT/US2018/047617.

* cited by examiner

CELL SORTER IN A SEALED SYSTEM UNDER CONTROLLED ATMOSPHERE

CROSS-REFERENCE TO RELATED APPLICATIONS

This application is a U.S. national counterpart application of international application serial No. PCT/US2018/047617, filed Aug. 22, 2018 which claims priority to U.S. Provisional Patent Application No. 62/548,953 filed Aug. 22, 2017, the disclosures of both of which are incorporated herein by reference in their entireties.

FIELD OF THE DISCLOSURE

The present disclosure relates generally to an apparatus that can provide a sealed chamber system capable of, including but not limited to, allowing for various oxygen tensions of choice to be maintained during cell harvest, sorting (and isolation of sorted subpopulations), analysis, etc.

BACKGROUND

Previous publications show that cells change very quickly (~10 minutes or less) when exposed to room air conditions rather than their native hypoxic environment. By not having an apparatus that is able to maintain such hypoxic conditions throughout, testing of such cells may lack robustness. More specifically, most tissues and organs in the body are found in low oxygen (O2)/hypoxic conditions, ranging in oxygen levels from 1-9% including the hematopoietic stem cell niche (1-5% O2). However, most experiments are conducted under room air conditions (20% O2) with samples returned to hypoxic conditions at later points during experimentation to determine the implications of hypoxia. Harvesting cells under hypoxic conditions can lead to an increase in multiple sub-populations of cells including phenotypic and functional stem cells as compared to harvesting in ambient air, in both hematopoietic and other cell types. Mimetics of pathways that are modified by hypoxia, such as CyclosporinA (CSA) (which binds to Cylophylin D and blunts the opening of Mitochondrial Permeability Transition Pore, MPTP) and subsequent induction of reactive oxygen species ((ROS) and ROS induced ROS release) mimicked only some of the phenotypic and functional effects of low oxygen tension (hypoxia), its effects are not enhanced under hypoxia. Additionally, there are many markers and functions (e.g., Dipeptidyl Peptidase 4 (DPP4) expression and activity) that are not retained by CSA, further demonstrating that the CSA only modifies a subset of the pathways that are facilitating the hypoxia phenotypes and functions detected.

We have determined that other factors and pathways, including but not limited to DPP4 for example, can also mimic some of the phenotypic and functional effects of hypoxia, but in a non CSA and non ROS dependent manor. As the pathways affected by hypoxia are multifaceted and broad, inhibition of a singular mechanism or pathway may not mimic all of the phenotypic and functional effects. To that end, studies to fully understand the basic biology and potential clinical application of the native low oxygen environment are imperative, and require the ability to isolate specific subpopulations of cells for further analysis. Isolation of stem cells (whose frequency can be $\frac{1}{10,000}$) and other novel subpopulations that may be detected or enhanced under hypoxia require multiple markers to identify them. Therefore, there is a need to be able to specifically identify and isolate, these cells to fully phenotypically and functionally investigate subpopulations of normal and malignant cells (via transplant, in vitro studies, etc.) under low oxygen or other controlled oxygen tensions and conditions to understand and test their biology and clinical/therapeutic implications.

SUMMARY OF THE DISCLOSURE

According to an embodiment of the present disclosure, a sealed chamber is provided. The sealed chamber includes: at least one processing chamber, wherein one of the processing chambers includes a cell sorter, wherein the at least one processing chamber includes an extended glove front coupled to and extending from a front face of the at least one processing chamber, the extended glove front comprising a door coupled to the front face and a pair of gloves extending inwardly into the at least one processing chamber; wherein the sealed chamber is a sealed system such that cells can be placed under consistent conditions such that cells can be sorted, obtained, and analyzed under consistent conditions.

In another particular embodiment, the at least one processing chamber includes one other processing chamber that includes a door hingedly coupled to a front face of the one other processing chamber, the door further including a single glove in the door, the single glove extending inwardly into the fourth processing chamber. In another particular embodiment, the sealed chamber further includes at least one buffer module adjacent to the at least one processing chamber, wherein the at least one buffer module includes a first buffer module and a second buffer module, the first and second buffer modules are both adjacent to the at least one processing chamber. In another particular embodiment, the sealed chamber further includes an incubator bank module adjacent to the at least one processing chamber, wherein the incubator bank module is coupled to a controller, wherein the controller manages the conditions within the at least one incubation chamber. In yet another particular embodiment, the extended glove front extends from the front face of the at least one processing chamber by between 0.25 inches to 2 inches.

In another particular embodiment, the at least one processing chamber includes a first processing chamber, a second processing chamber, a third processing chamber, and a fourth processing chamber; the at least one buffer module includes a first buffer module, a second buffer module, and a third buffer module; and the first processing chamber is adjacent to the first and second buffer modules, the second processing chamber is adjacent the second and third buffer modules, and the third processing module is adjacent to the third buffer module and the fourth processing chamber. In another particular embodiment, the incubator bank module is adjacent to the second processing chamber. In another particular embodiment, the sealed chamber further includes a plurality of apertures in a rear face of the at least one processing chamber configured to receive cables of additional processing units, wherein the additional processing units function to maintain operating conditions of the sealed chamber. In yet another particular embodiment, at least one of the buffer modules include a side door configured to allow for the injection of test subjects within the sealed chamber.

In another embodiment, a sealed chamber is provided. The sealed chamber includes a first processing chamber, a second processing chamber, a third processing chamber, and a fourth processing chamber; and wherein the third processing chamber includes an extended glove front coupled to and extending from a front face of the at least one processing chamber, the extended glove front comprising a door coupled to the front face and a pair of gloves extending inwardly into the at least one processing chamber and a plurality of apertures in a rear face of the at least one processing chamber configured to receive cables of additional processing units, wherein the additional processing units function to maintain operating conditions of the sealed chamber; wherein the fourth processing chamber includes a door hingedly coupled to a front face of the fourth processing chamber, the door further including a single glove in the door, the single glove extending inwardly into the fourth processing chamber.

In another particular embodiment, the sealed chamber further includes at least one buffer module includes a first buffer module, a second buffer module, and a third buffer module; wherein the first processing chamber is adjacent to the first and second buffer modules, the second processing chamber is adjacent the second and third buffer modules, and the third processing module is adjacent to the third buffer module and the fourth processing chamber. In another particular embodiment, the sealed chamber further includes an incubator bank module adjacent to at least one of the processing chambers; wherein the incubator bank module is coupled to a controller, wherein the controller manages the conditions within the at least one incubation chamber. In yet another particular embodiment, the incubator bank module is adjacent to the second processing chamber. In yet another particular embodiment, the extended glove front extends from the front face of the at least one processing chamber by between 0.25 inches to 2 inches. In yet another particular embodiment, the cell sorter is a sealed system such that cells can be placed under consistent conditions such that cells can be sorted, obtained, and analyzed under consistent conditions. In yet another particular embodiment, at least one of the buffer modules is configured to have the ability to introduce room air to allow test subjects to breathe room air, wherein at least one of the buffer modules further includes a side door configured to allow for the injection of test subjects within the sealed chamber. In yet another particular embodiment, the sealed chamber is maintained under hypoxic conditions and is a sealed system.

Additional features and advantages of the present disclosure will become apparent to those skilled in the art upon consideration of the following detailed description of the illustrative embodiment exemplifying the best mode of carrying out the disclosure as presently perceived.

BRIEF DESCRIPTION OF THE DRAWINGS

The foregoing aspects and many of the intended advantages of this disclosure will become more readily appreciated as the same becomes better understood by reference to the following detailed description when taken in conjunction with the accompanying drawings, wherein.

Figure 1:
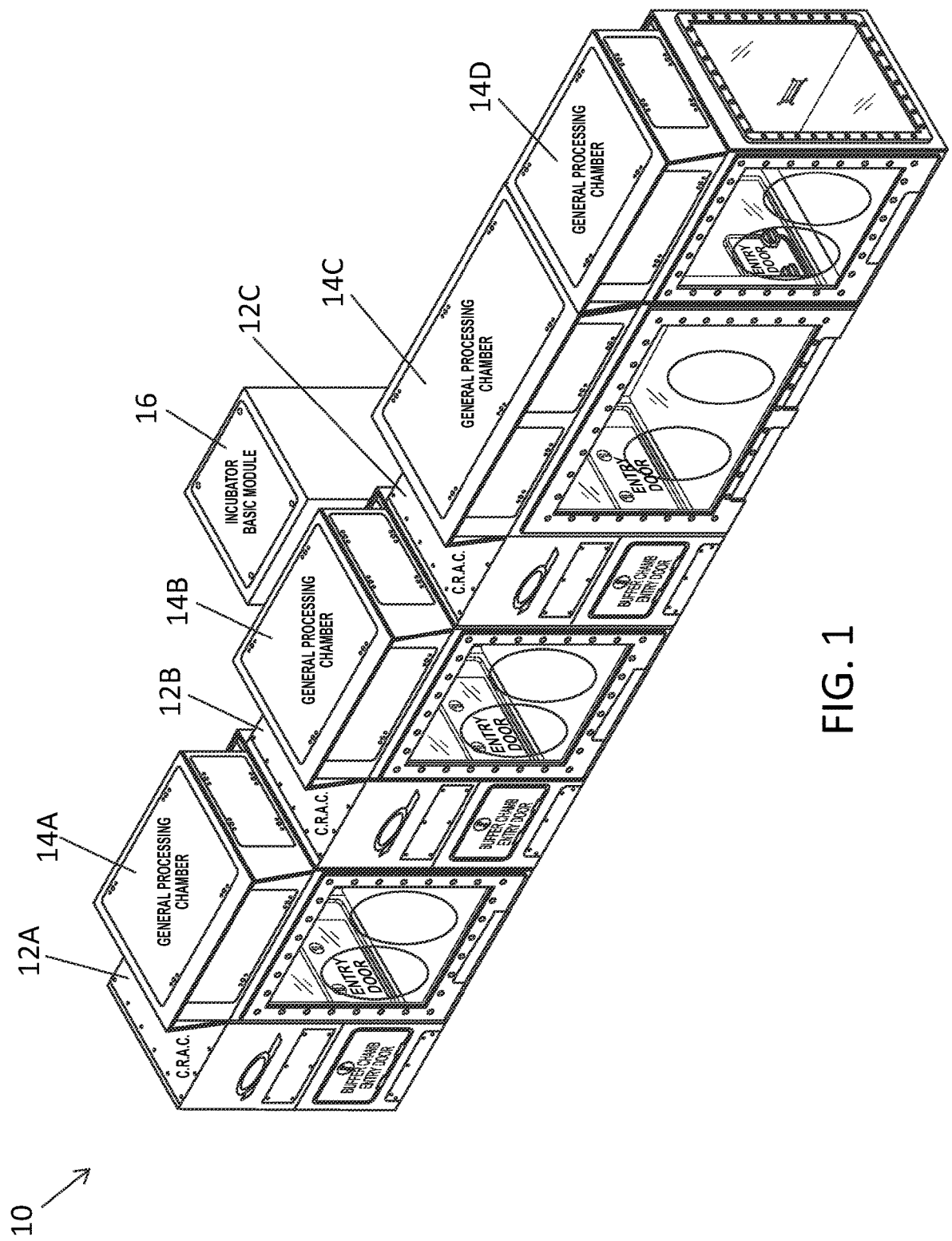
FIG. 1 is a perspective view of a sealed chamber in accordance with the present disclosure.

Corresponding reference characters indicate corresponding parts throughout the several views. Although the drawings represent embodiments of various features and components according to the present disclosure, the drawings are not necessarily to scale and certain features may be exaggerated in order to better illustrate and explain the present disclosure. The exemplifications set out herein illustrate embodiments of the disclosure, and such exemplifications are not to be construed as limiting the scope of the disclosure in any manner.

DETAILED DESCRIPTION OF THE DRAWINGS

For the purposes of promoting an understanding of the principals of the disclosure, reference will now be made to the embodiments illustrated in the drawings, which are described below. The embodiments disclosed below are not intended to be exhaustive or limit the disclosure to the precise form disclosed in the following detailed description. Rather, the embodiments are chosen and described so that others skilled in the art may utilize their teachings. It will be understood that no limitation of the scope of the disclosure is thereby intended. The disclosure includes any alterations and further modifications in the illustrative devices and described methods and further applications of the principles of the disclosure which would normally occur to one skilled in the art to which the disclosure relates.

Figure 2:
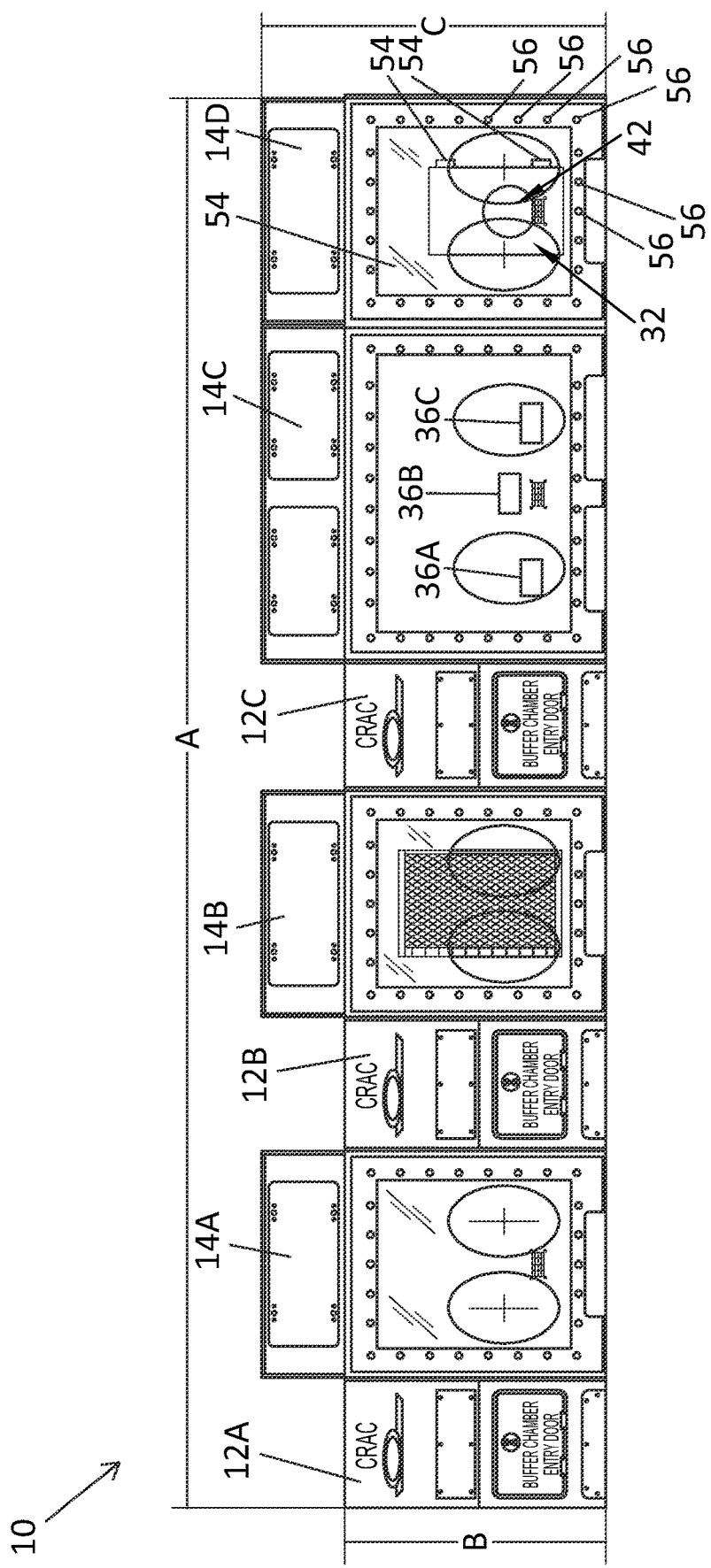
FIG. 2 is a front elevational view of the sealed chamber of FIG. 1 with some modifications including apertures on a rear face of a processing chamber and a door on a front face of another chamber.
Figure 3:
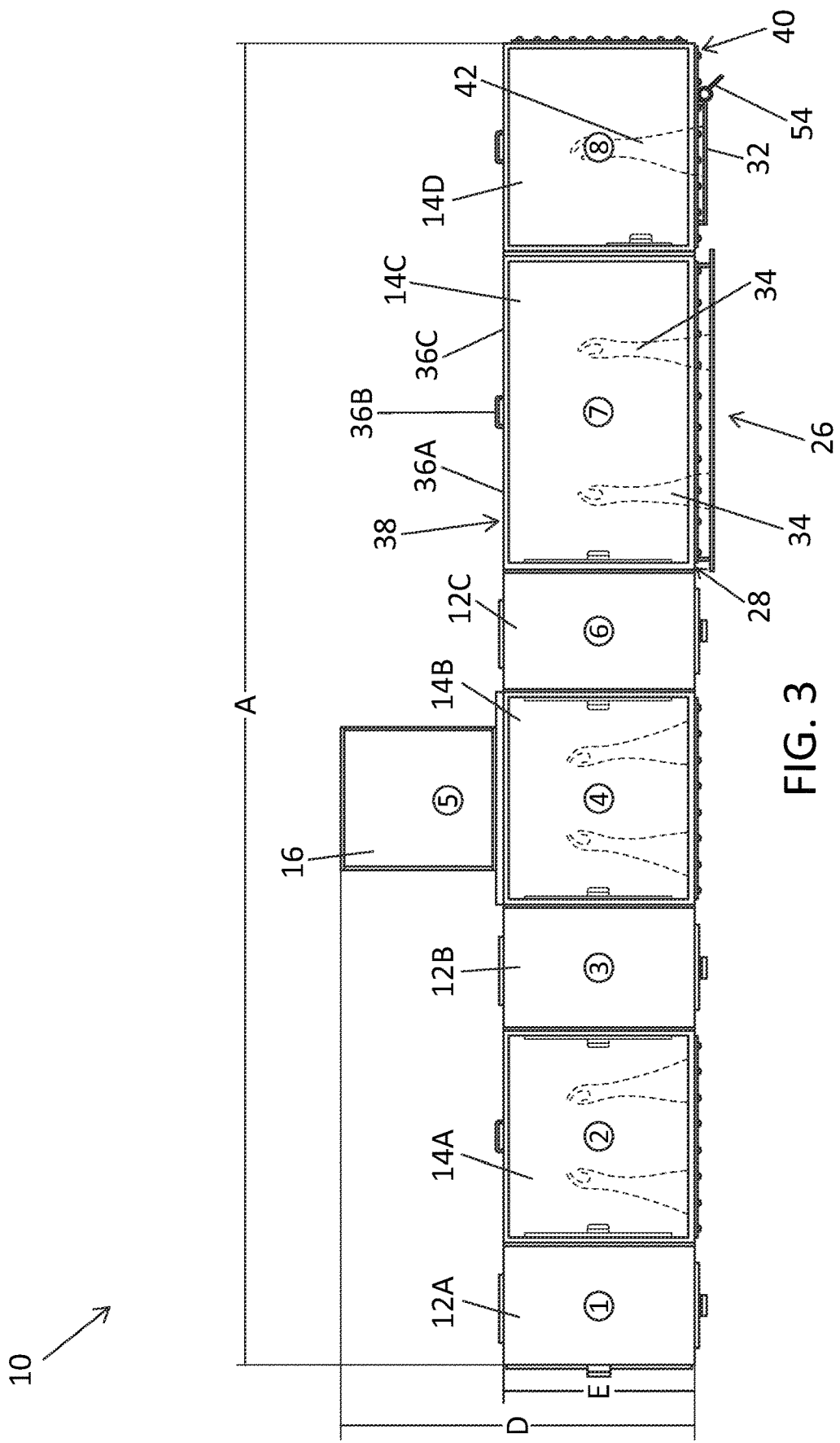
FIG. 3 is a top plan view of a modified sealed chamber of FIG. 2 illustrating the alterations made to the sealed chamber shown in FIG. 1.

Referring to FIGS. 1-3, a sealed chamber 10 is shown. Sealed chamber 10 includes processing chambers 14A-D, buffer modules 12A-C, and an incubator bank module 16. As shown in FIGS. 1-3, processing chamber 14A is adjacent to and coupled to buffer modules 12A and 12B, processing chamber 14B is adjacent to and coupled to buffer modules 12B and 12C, processing chamber 14C is between and coupled to buffer module 12C and processing module 14D, and incubator bank module 16 is adjacent to and coupled to processing chamber 14B. The buffer modules 12A-C, processing chambers 14A-D, and incubator bank module 16 are fluidly connected to each other such that a sample may pass from one unit to another without a significant change in conditions. It is within the scope of the present disclosure that an alternate configuration of buffer modules 12A-C, processing chambers 14A-D, and incubator bank module 16 are possible. In an exemplary embodiment, a test subject (e.g., mice or other animal(s)) is included in sealed chamber 10 to allow for injection of sorted cells (at multiple sites) or harvesting of blood etc. from the test subjects (of multiple sizes) and retaining the samples under low oxygen tension while also allowing for appropriate, dark/less stressful conditions for the test subject and room air (or atmospheric conditions, approximately 21% O2 for the test subjects (e.g., animals) to breathe) supplied next to the test subject. The configuration of sealed chamber 10 enables for the test subjects to be moved or positioned within sealed chamber 10 as needed. The configuration also allows for injections, blood draws, etc. of the test subjects to be completed by a single person/operator/experimenter.

Referring to FIGS. 2 and 3, where a modified sealed chamber 10 of FIG. 1 is provided, buffer modules 12A-C and processing chambers 14A-D span a distance A from an outer edge of buffer module 12A to an outer edge of processing module 14D as shown. Distance A may range from about 150 inches to 250 inches, or from about 190 inches to 200 inches. In the illustrated embodiment, distance A is about 199⅜ inches. In an alternate embodiment, distance A is about 199 inches. In a further alternate embodiment, distance A is 200 inches. Further, distance D (FIG. 3) represents the distance spanned by processing chamber 14B and adjacent incubator bank module 16. Specifically, distance D represents the distance from a forward edge of incubator bank module 16 to a rearward edge of processing chamber 14B. Distance D may range from about 25 inches to 75 inches, or from about 50 inches to 60 inches. In the illustrated embodiment, distance D is about 52 inches. Also, distance E (FIG. 3) represents the distance spanned by the lengths of buffer modules 12A-C and processing chambers 14A-D (i.e. from a forward edge of buffer modules 12A-C and processing chambers 14A-D to a rearward edge of buffer modules 12A-C and processing chambers 14A-D). Distance E may range from about 10 inches to 50 inches, or from about 20 inches to 30 inches. In the illustrated embodiment, distance E is about 28 inches. It is within the scope of the present disclosure that distances A-E may further vary depending on the application.

Additionally, as shown in FIG. 2, distances B and C represent the heights of buffer modules 12A-C and processing chambers 14A-D, respectively. Distance B may range from about 20 inches to about 50 inches, or from about 30 inches to 40 inches. Distance C may range from about 30 inches to about 70 inches, or from about 40 inches to about 60 inches.

Figure 4:
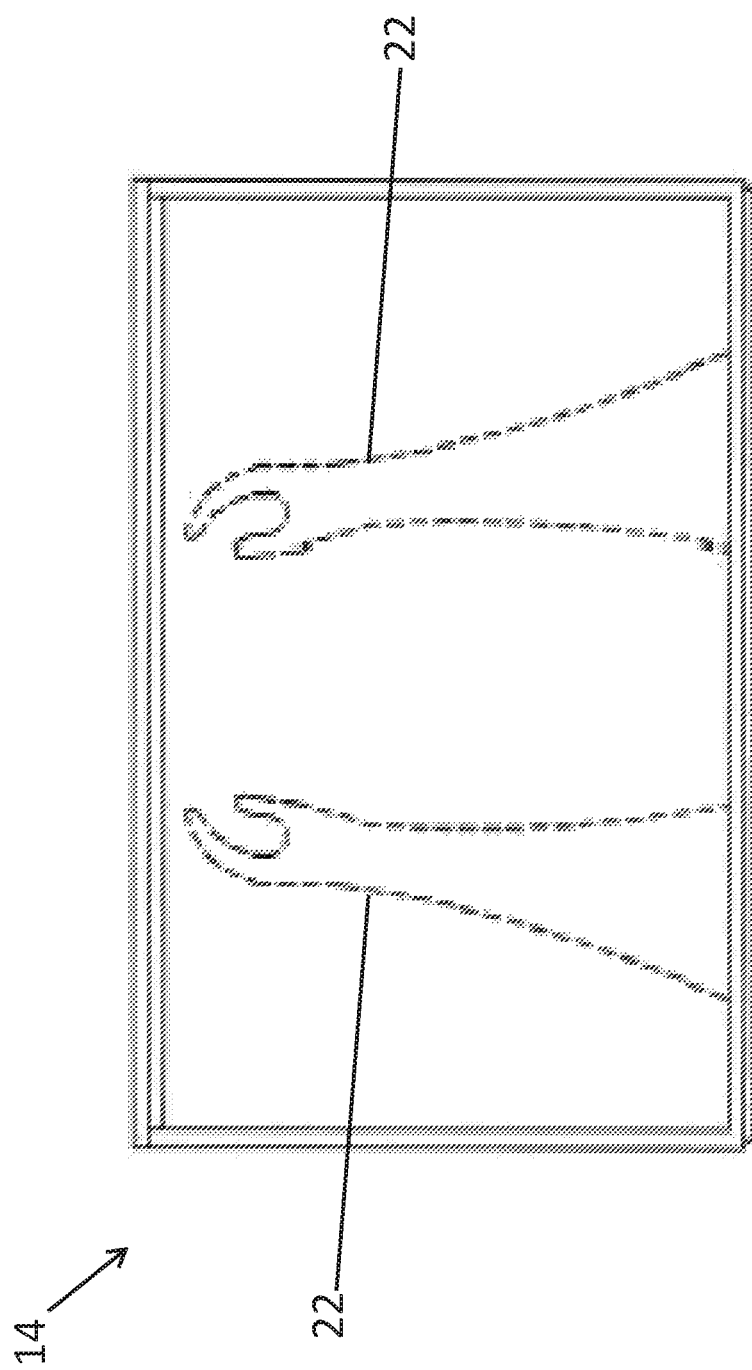
FIG. 4 is a top plan view of a processing chamber for the sealed chamber of FIG. 1.

Processing chambers 14A-D function to provide a chamber to hold samples and prepare them for various processing needs and testing conditions (e.g., varying oxygen content, CO2 control, temperature control, hepafiltration, etc.) so that the cells are consistently contained in the appropriate, desired oxygen tension. Processing chambers 14A-D may also contain specified third party processing equipment, which is operated through gloves 22 (FIG. 4) that protrude into chambers 14A-D. The chambers 14A-D further include doors that permit communication between adjacent units (e.g., buffer chambers 12A-C, an adjacent processing chamber, or incubation bank module 16). and may also include buffer chambers 12A-C and the aforementioned glove system 22 to allow for the maintenance of desired oxygen tension or other conditions during cell harvest, processing, sorting, transplantation, animal handling and assessment, as well as phenotypic and functional cell analysis.

Processing chambers 14A-D have exterior surfaces that are made from polymers such as polypropylene or polyvinylchloride. It is within the scope of the present disclosure that alternate polymers may be used for the exterior of the processing chambers 14A-D. The interior surfaces of processing chambers 14A-D are made from polypropylene with interior extending gloves being made from polyvinylchloride. It is within the scope of the present disclosure that alternate polymers or materials (e.g., stainless steel) may be used for the interior surfaces of processing chambers 14A-D.

Figure 8:
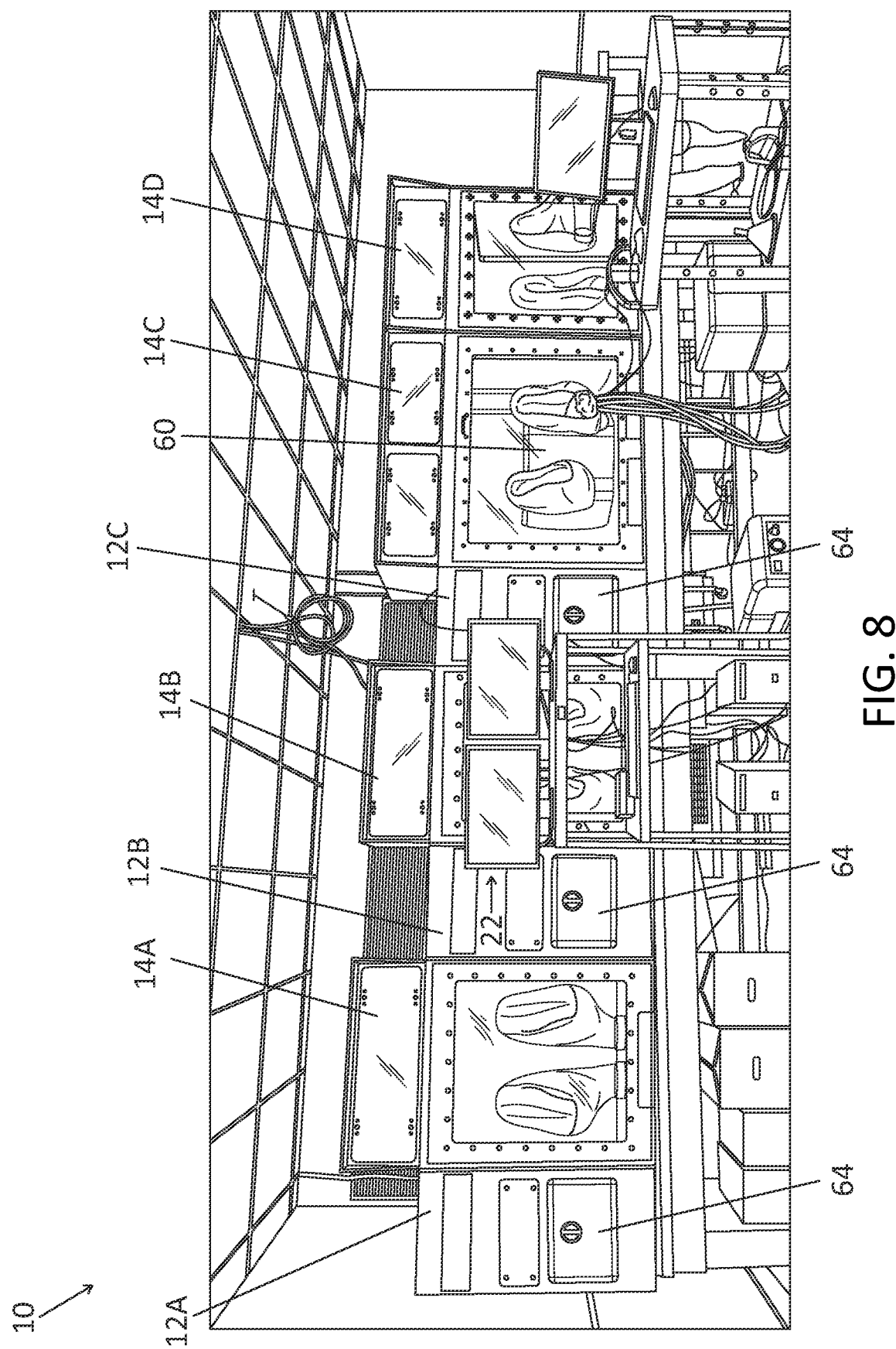
FIG. 8 is a side, perspective view of a portion of the modified sealed chamber of FIG. 2.
Figure 9:
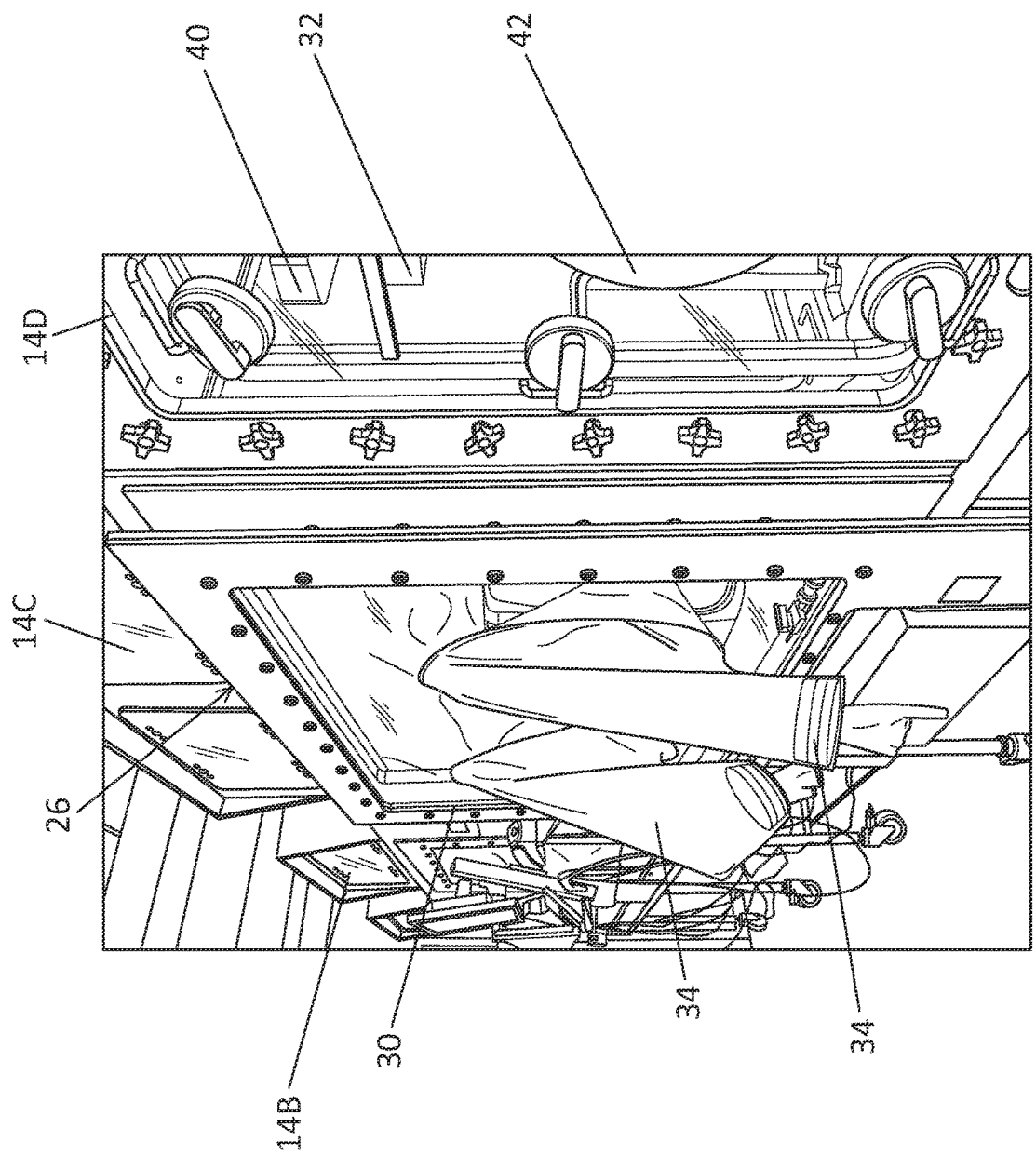
FIG. 9 is a side, perspective view of the portion of the modified sealed chamber of FIG. 9 illustrating modified processing chambers as discussed further herein.
Figure 10:
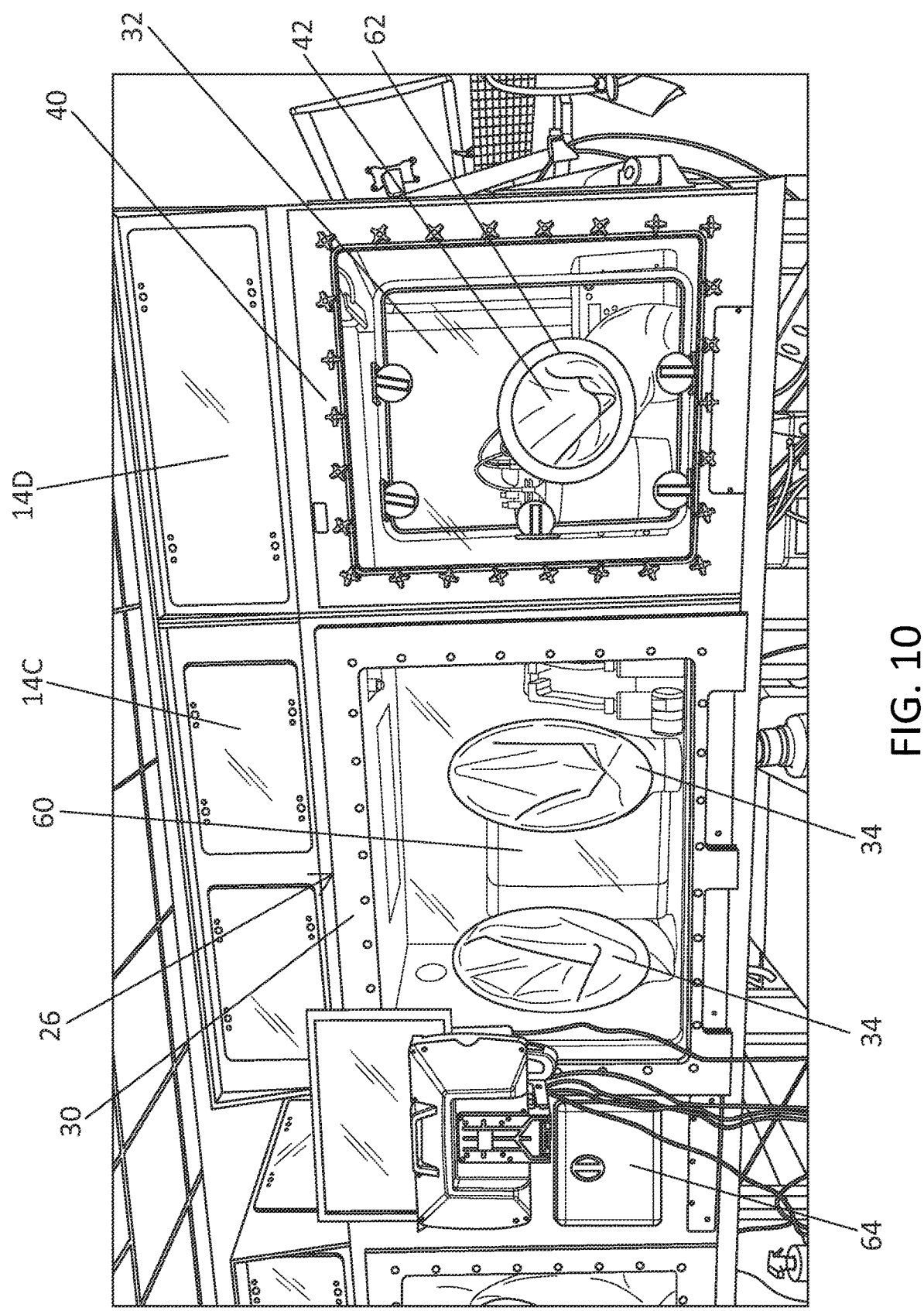
FIG. 10 is a side, perspective view of the portion of the modified sealed chamber and the modified processing chambers of FIG. 9.
Figure 11:
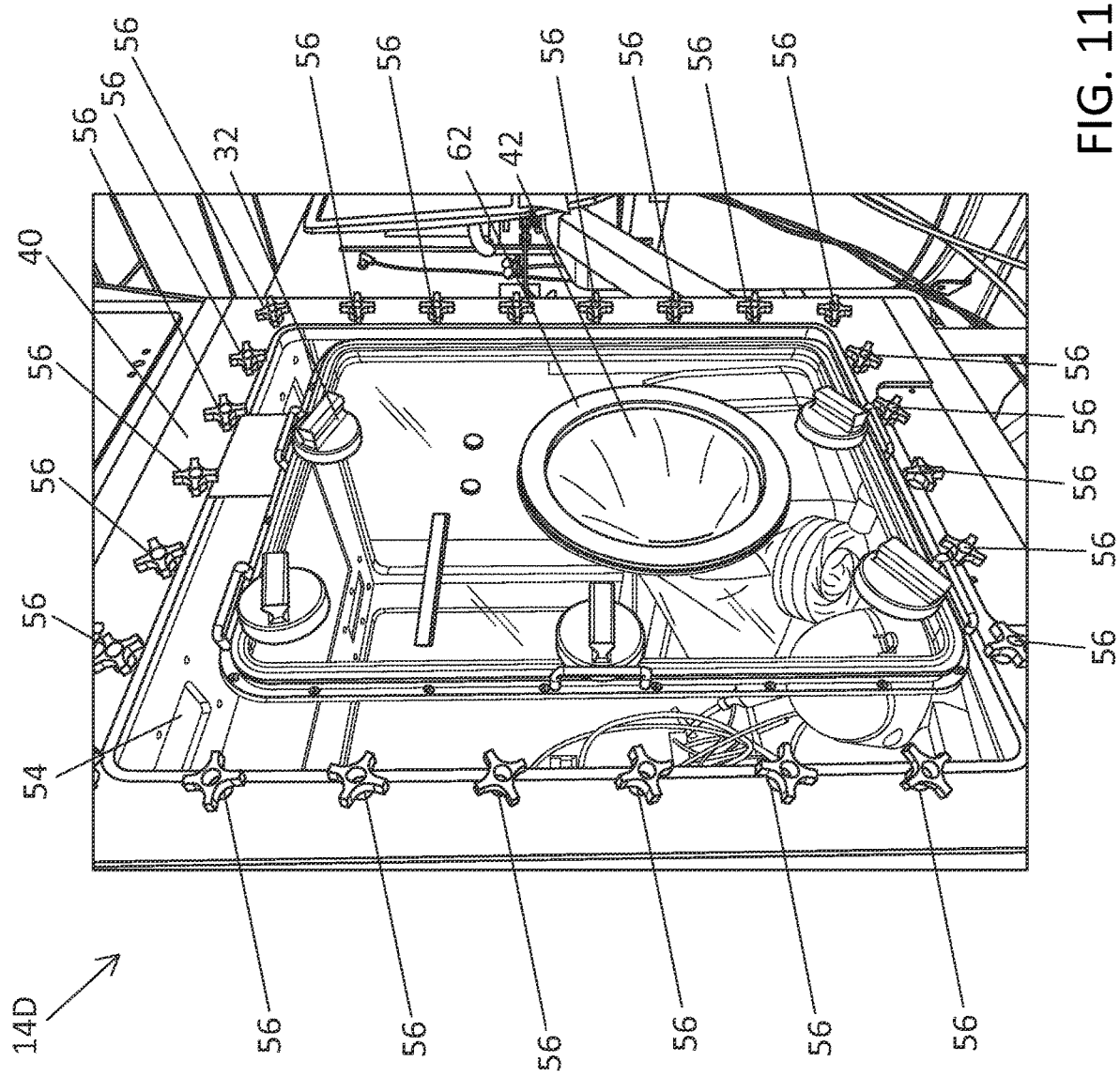
FIG. 11 is a side, perspective view of one of the modified processing chambers of the modified sealed chamber of FIG. 2.
Figure 12:
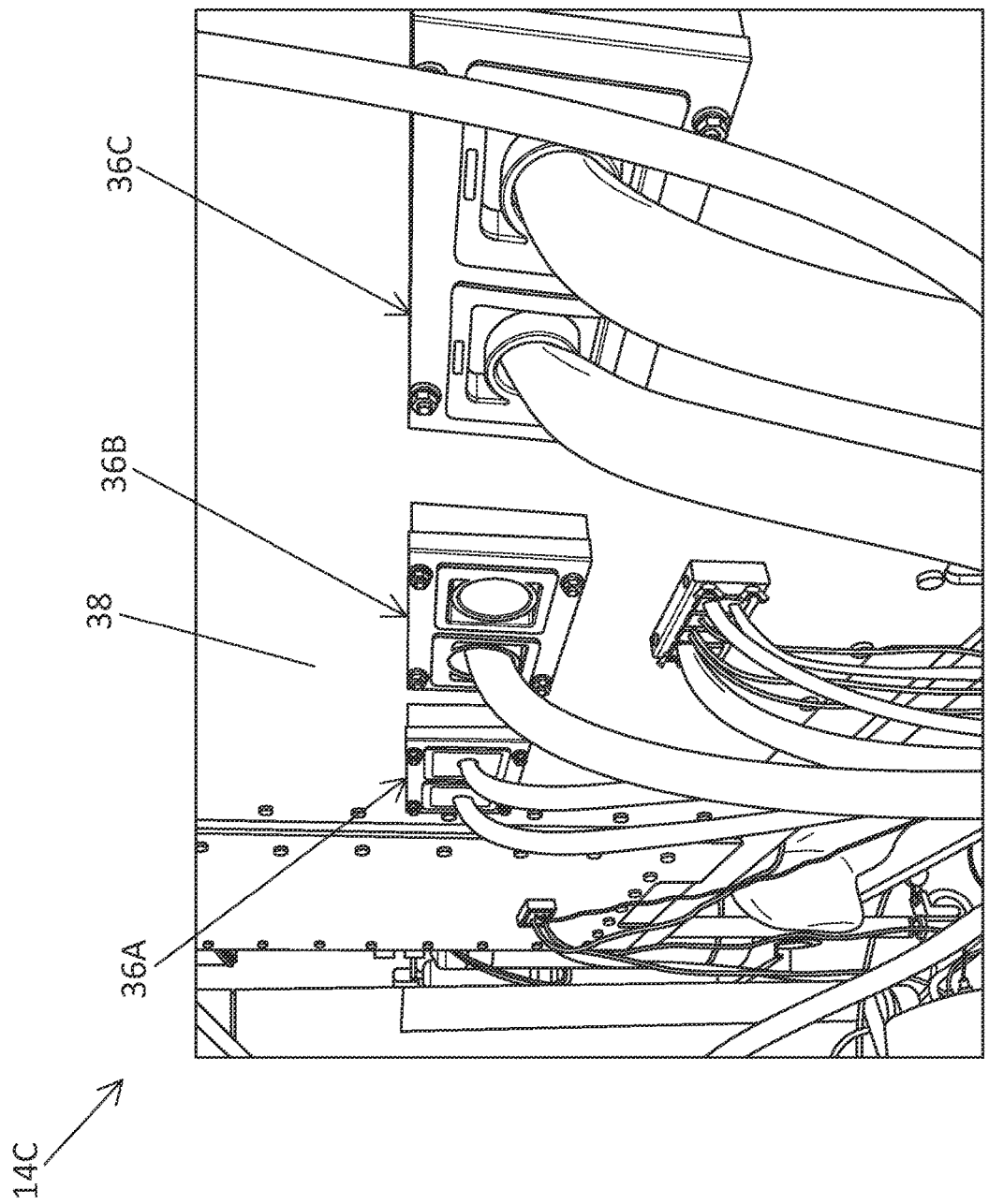
FIG. 12 is a perspective view of a rear side of one of the processing chambers of the modified sealed chamber of FIG. 10.

In an exemplary embodiment, processing chambers 14A-D function to include the following chambers: a chamber to hold, manipulate, and harvest from test subjects (e.g., mice), a "human" chamber for housing human cells with an incubator, a chamber modified to house a cell sorter 60 (FIGS. 8 and 10), and an additional chamber for housing additional experimental equipment or units (e.g., sorter fluids, centrifuge, etc.). Further, in an exemplary embodiment, processing chamber 14A provides a test subject chamber (e.g., mice or other animals) that allows for injection via multiple methods as well as other sampling (e.g., blood sampling, etc.) in a manner that allows the test subjects (mice or other animals) to breathe air, but the cells that are injected or removed can be under low oxygen tension. As discussed further herein, chambers 14C and 14D include modifications for depth and function to allow for interaction with the sorter and its components, as well as appropriate function.

As shown in FIGS. 1-3, processing chambers 14A-D vary in size. Processing chambers 14A-D may have a width ranging from about 20 inches to 70 inches, or from about 30 inches to 60 inches. In one embodiment, processing chambers 14A, 14 B, and 14D are 32 inches in width, and processing chamber 14C is 47 inches in width. However, it is within the scope of the present disclosure that alternate widths of processing chambers may be used, such as, for example, 52 inches.

As further shown in at least FIGS. 2 and 3 and also FIGS. 9-12, processing chambers 14C and 14D include additional features. Processing chamber 14C further includes an extended glove front 26 coupled to a front side 28 of chamber 14C. Extended glove front 26 extends between 0.25 inches to 2 inches from front side 28 of chamber 14C. In one embodiment, extended glove front 26 extends 0.5 inches from front side 28. Extended glove front 26 includes a door 30 coupled to chamber 14C and included in door 30, are gloves 34 that extends inwardly into chamber 14C. Door 30 functions to maintain the specified airflow conditions, provide space for interaction with the cell sorter 60 (FIGS. 8 and 10) and opening of sorter door, parts, and function, and minimize vibrations through processing chamber 14C. The functionality of sealed chamber 10 is sensitive to air flow conditions and vibration within chamber 14C. As such, door 30 provides a seal to processing chamber 14C such that specified air flow conditions are maintained and vibrations are reduced within processing chamber 14C to allow for proper sorting. Furthermore, such a configuration provides space for interaction with cell sorter 60 required for stream set up, maintenance, function/operation, and sample handling. In one embodiment, door 30 is made from polypropylene or polyvinylchloride. However, it is within the scope of the present disclosure that alternate suitable materials may be used for door 30.

Processing chamber 14C also includes additional apertures 36 A, B, C on back side 38. Additional apertures 36A, 36B, and 36C enable additional units to be connected (via cables fed through apertures 36A, 36B, and 36C) to processing chamber 14C to maintain specific operating conditions (e.g., oxygen content) within chamber 14C without potential damage to the cables during operation of sealed chamber 10. For example, in one embodiment, additional apertures 36A, 36B, and 36C enable units responsible for aerosol management options (AMO), waste fluidics, sorter cooler, pressurization requirements, etc. to be connected to processing chamber 14C. In another exemplary embodiment, waste tanks are positioned outside sealed chamber 10 and the lines connecting the waste tanks to processing chamber 14C are fed through at least one of apertures 36A, 36B, and 36C to connect the waste tanks to processing chamber 14C. Apertures 36A, 36B, and 36C vary in size from between 1"×4" to 5"×8" each. In one embodiment, each aperture 36A, 36B, and 36C is 3"×6".

Processing chamber 14D includes a plate 54 coupled to front side 40 by multiple hinges 56. Plate 54 further includes a hinged door 32 hingedly coupled to plate 54 and front side 40 by a set of hinges 52. Hinged door 32 includes a single interior extending glove 42 with a glove opening 62 in door 32. Hinged door 32 is of a solid construction. In one embodiment, hinged door 32 is made of plexiglass. However, it is within the scope of the present disclosure that other suitable plastic or plastic composite materials may be used for hinged door 32. In one embodiment, hinged door 32 is approximately 18"×24". However, it is within the scope of the present disclosure that other suitable sizes of hinged door 32 may be used. In another embodiment, glove opening 62 comprises a 9 inch diameter opening with a glove extending therefrom. However, it is within the scope of the present disclosure that alternate suitable opening shapes and sizes may be used.

Similar to door 30, door 32 functions to maintain the specified airflow conditions and minimize vibrations through processing chamber 14D. The cell sorting functionality of sealed chamber 10 is sensitive to air flow conditions and vibration within chamber 14D. As such, door 32 provides a seal to processing chamber 14D such that specified air flow conditions are maintained and vibrations are reduced within processing chamber 14D to allow for proper sorting. The configuration of processing chamber 14D enables the configuration of necessary pressure and fluidics for the cell sorter as well as the ability to add or modify sheath fluid. This allows for the fluidics/pressure within sealed chamber 10 and cell sorter 60 to be maintained at the appropriate O2 content for extended periods of time and for additional fluid to be added without disrupting O2 content during an experiment/cell sort. The configuration of the processing chamber also allows for easy addition of fluids, components, sheath containers etc. to the chamber without removal of the entire large panel and all of the knobs/hinges 56 on the processing chamber as discussed further herein.

In addition, hinges 52 are beneficial for maintenance of processing chamber 14D. That is, without hinges 52, when processing chamber needs to be maintained or cleaned (as it requires putting in a new sheath tank) all of hinges 56 would need to be removed. However, with hinges 52, maintenance of processing chamber is less taxing on the experimenter as fewer hinges 52 need to be removed. Further, any equipment added to chamber 14D would also require the removal and addition of all hinges 52 which can reduce the sealing effect of plate 54 and also impacts the O2 maintenance within sealed chamber 10 and processing chamber 14D over time.

Glove 42 with glove opening 62 in door 32 allows the experimenter to modify the O2 content of the fluidics, pressure, add sheath fluid, etc. within chamber 14D during an experiment while also maintaining the O2 tension within the sealed chamber 10. Moreover, the advantages of glove 42 with glove opening 62 are present in conjunction with the aforementioned advantages of door 32.

The additional features of processing chambers 14C, 14D alter the depth of the chambers. That is, processing chambers 14A, 14B have a depth that ranges from between 25 inches to 45 inches, and processing chambers 14C, 14D have a depth that ranges from between 30 inches to 50 inches. In an exemplary embodiment, processing chambers 14A, 14B have a depth between approximately 30 inches and 35 inches, and processing chambers 14C, 14D have a depth between approximately 35 inches to 38 inches.

Figure 13:
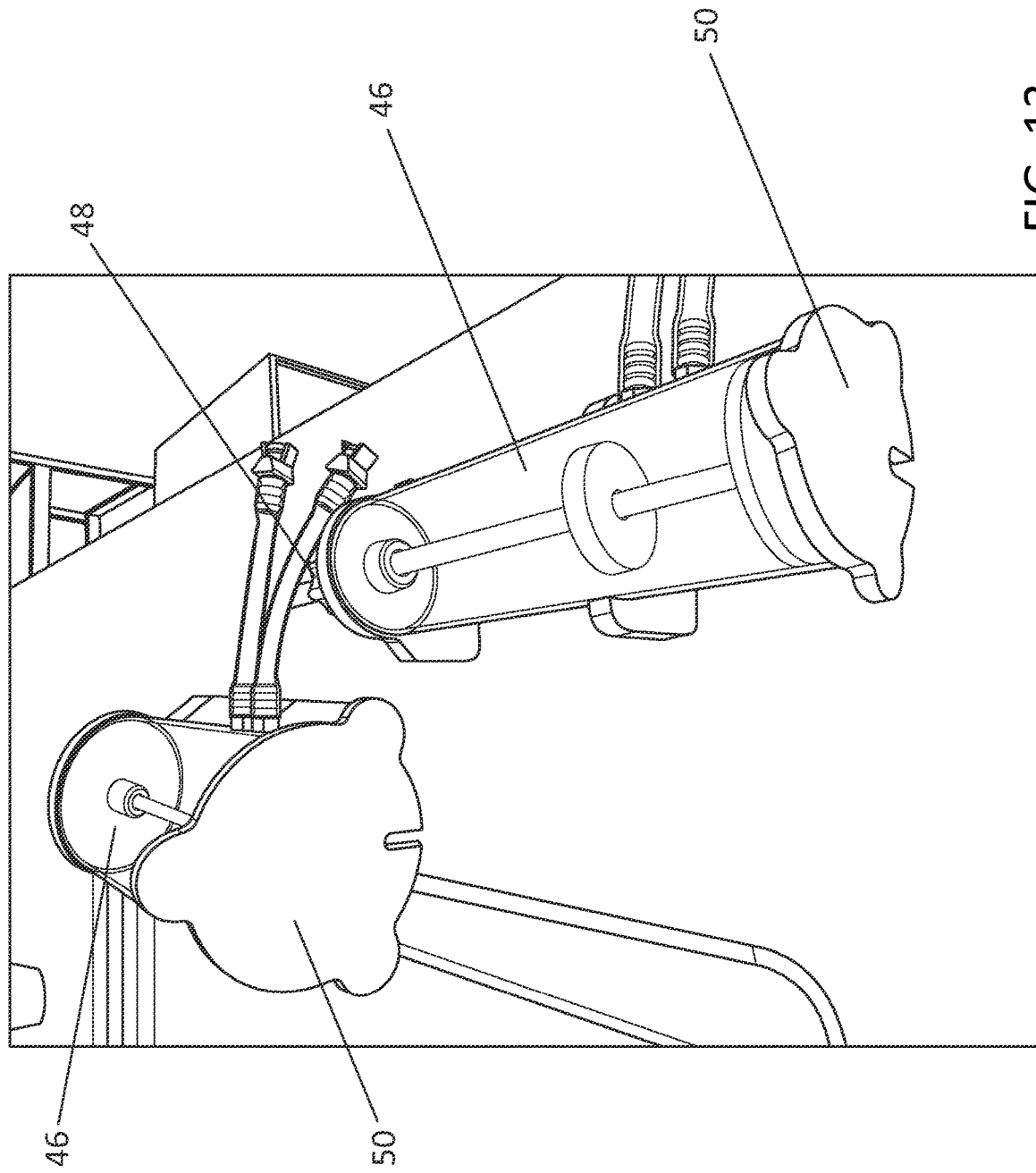
FIG. 13 is a perspective view of a test subject holder used with the modified sealed chamber of FIG. 9.
Figure 14:
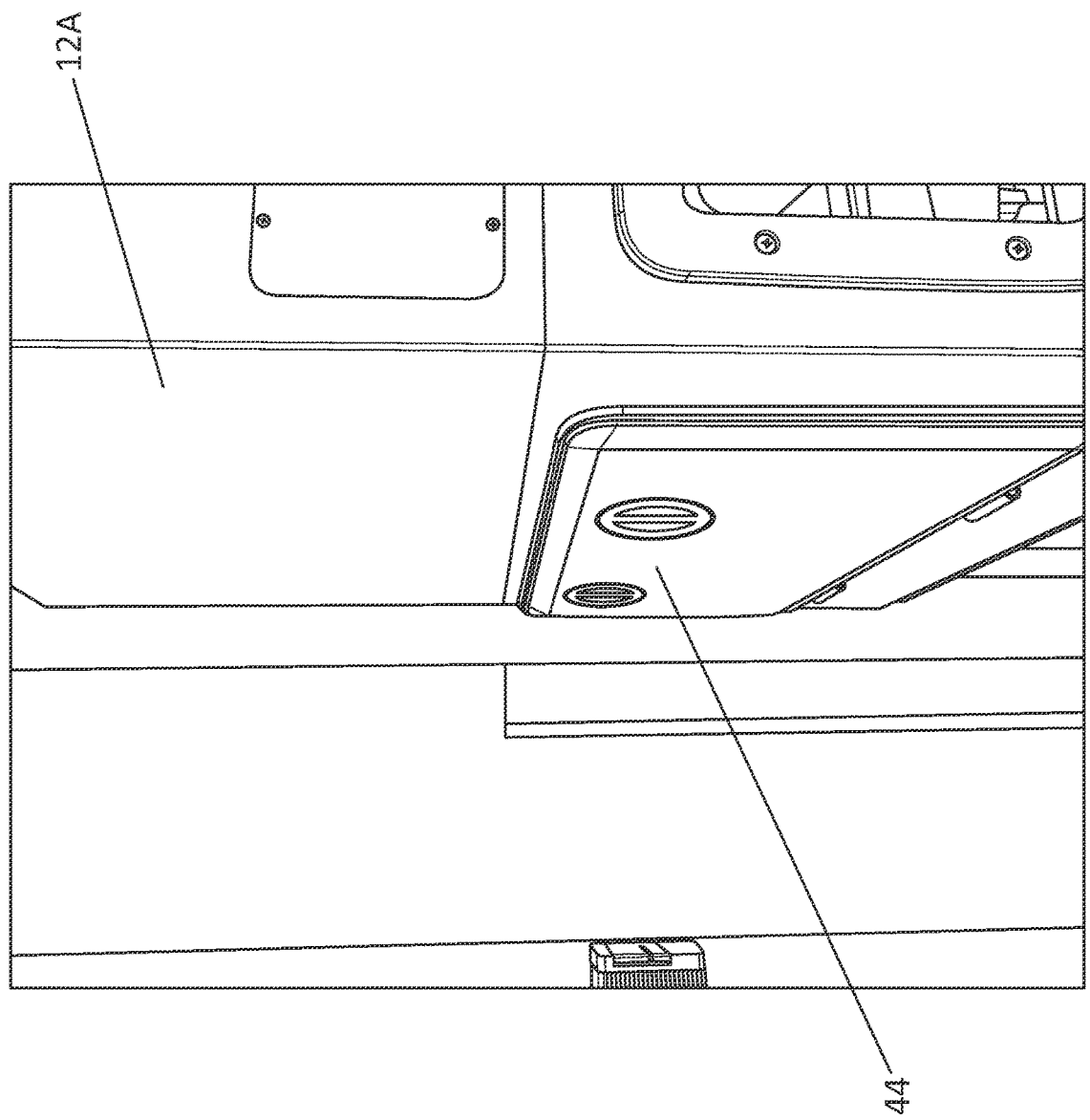
FIG. 14 is a perspective view of a portion of a buffer chamber of the modified sealed chamber of FIG. 9.

Buffer modules 12A-C offer an air lock seal between the interior of the respective module 12A-C and the external environment. One function of the buffer modules is to introduce room air and have room air specifically flow to the test subjects such that the test subjects can breathe room air. Another function of the buffer modules is to provide a staging area for items entering and exiting the adjacent processing chambers 14A-D without compromising isolation. For example, as shown in FIG. 14, a side door 44 is provided on buffer module 12A that is used to insert the test subject(s) (e.g., mice) into sealed chamber 10 (via buffer module 12A). Also, doors 64 are provided on buffer modules 12A, 12B, and 12C (FIGS. 8 and 10) function similar to side door 44 and are used to insert the test subject(s) (e.g., mice) into sealed chamber 10 (via the respective buffer modules 12A, 12B, 12C). The test subjects can be placed in holders 46 (FIG. 13), which allow the test subjects to breathe during the injection process. Holder 46 includes a plunger 48 that allows for the test subject to be sequestered in a part of holder 46 to facilitate easier injection into sealed chamber 10. Holder 46 further includes removable cap 50 that is removed to put the test subjects within the buffer module of sealed chamber 10.

Figure 5:
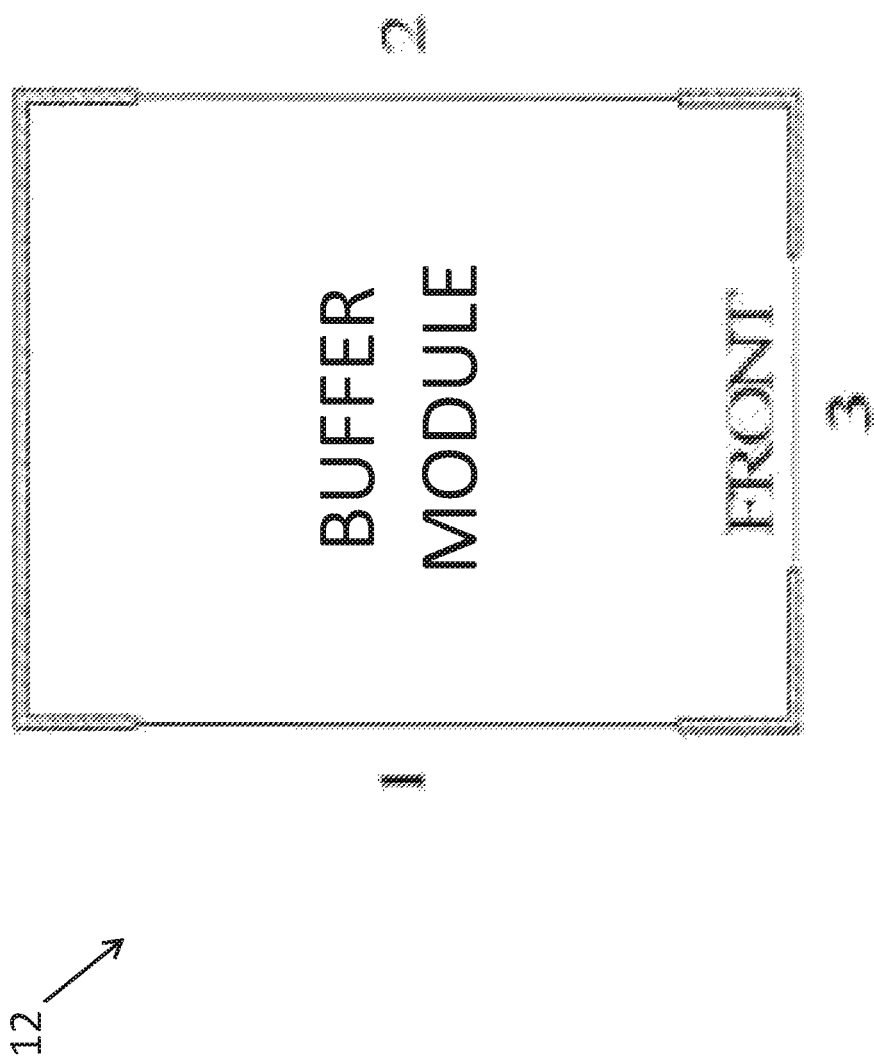
FIG. 5 is a top plan view of a buffer module for the sealed chamber of FIG. 1.

Another function of the buffer modules 12A-C is to expel the air that enters from the external environment by displacement with sterile filtered gas (at a specific O2 content) and also for optional variable log reduction of airborne particulates before opening inner door (e.g., purging). Another function of the buffer modules 12A-C is to replicate the oxygen atmosphere conditions of a neighboring workspace of a processing chamber. These conditions are established within the buffer module 12 before opening the inner door 1,2 (FIG. 5) of the buffer module to avoid disturbance in the workspace when inner doors 1 or 2 are opened. Buffer modules 12A-C may also monitor pressure in a similar manner as described for the replication of oxygen atmospheric conditions above. Further, the buffer modules 12A-C may function to provide a barrier opening between high particle generating equipment (e.g., a centrifuge) in one processing chamber 14A-D and another processing chamber 14A-D where cells may reside or be exposed (e.g., a cell sorter 60 (FIGS. 8 and 10)). In some instances, a buffer module 12A-C can take care of particle generation and particles can be purged out if needed.

Buffer modules 12A-C have exterior surfaces that are made from polymers such as polypropylene or polyvinylchloride. The interior surfaces of buffer modules 12A-C are made from polypropylene with interior extending gloves being made from polyvinylchloride. It is within the scope of the present disclosure that alternate polymers or materials (e.g., stainless steel) may be used for the exterior surfaces and/or the interior surfaces of buffer modules 12A-C.

As mentioned earlier and shown in FIGS. 1-3, processing chamber 14B is positioned adjacent to and coupled to incubator bank module 16. One function of incubator bank module 16 is to hold 1-3 incubation chambers and control the temperature to a uniform homogeneous temperature within these chambers. The incubation chambers can be covered by an insulated door frame and door 24 and can open into the room. Alternatively, the incubation chambers can be enclosed by a processing chamber (e.g., processing chamber 14B) such that the incubation chambers only open into the processing chamber. Further, the incubator bank module 16 functions to provide short-term experimental incubations in order to maintain oxygen tension and temperature conditions. The incubator module 16 can also provide long-term experimental incubations for long term assays, such as colony assays or ex vivo expansion so the cells do not have to leave the ideal oxygen condition/tension.

Figure 6:
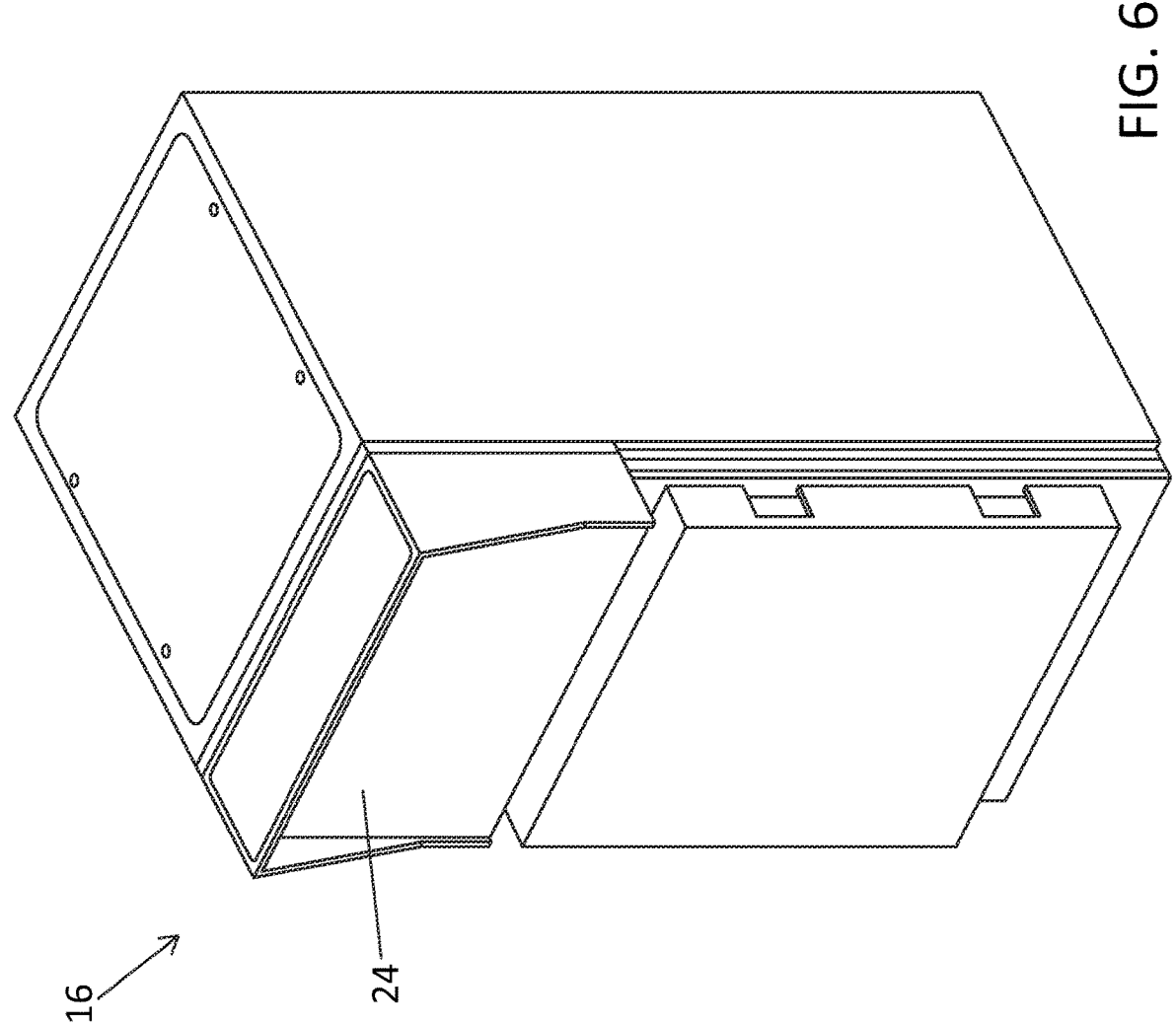
FIG. 6 is a perspective view of an incubator bank module with its door frame and doors attached.
Figure 7:
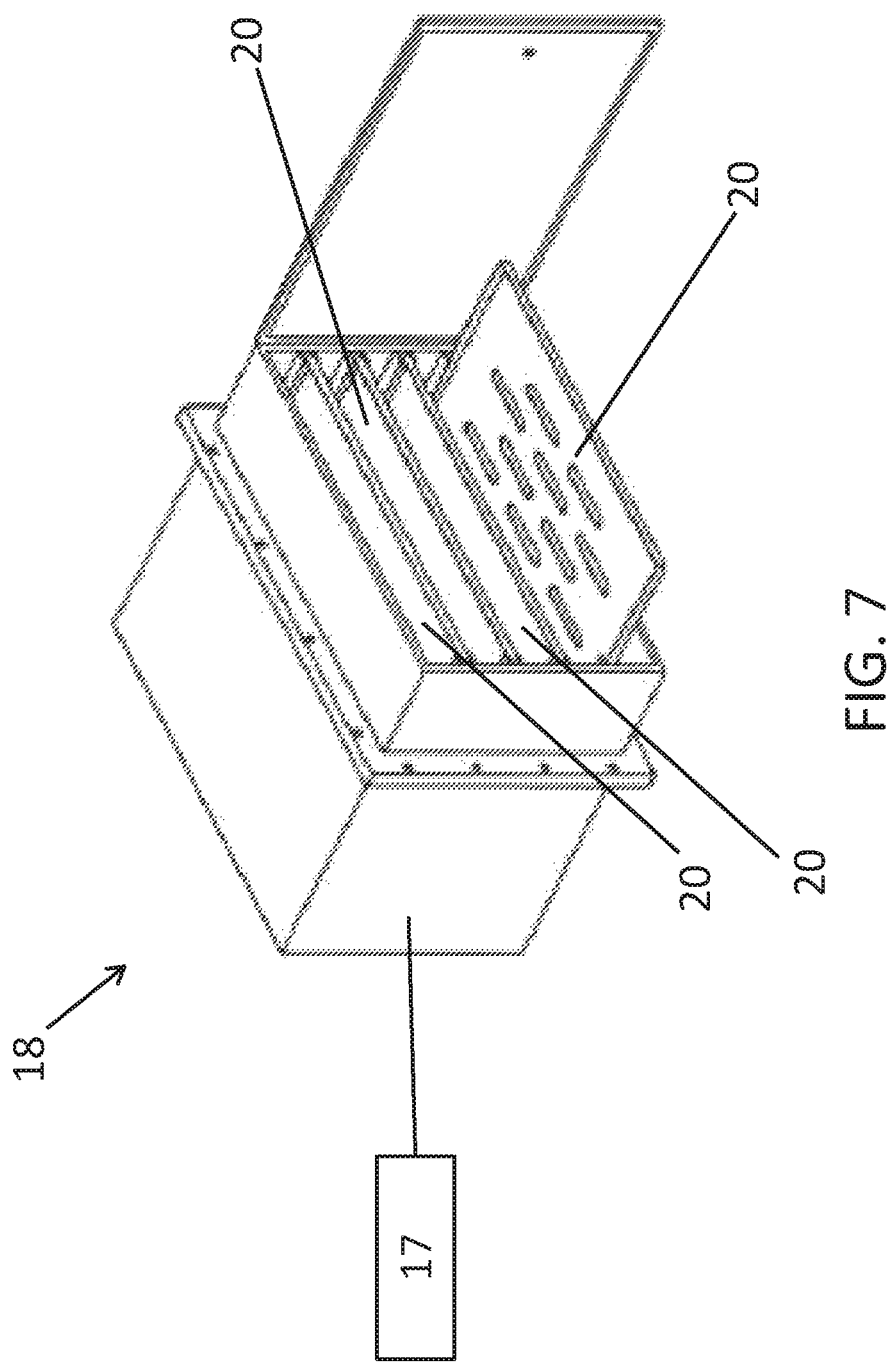
FIG. 7 is a perspective view of an incubation chamber that is positioned within the incubator bank module of FIG. 6.

As mentioned previously, incubator bank module 16, as shown in FIG. 6, includes at least one incubation chamber 18 (FIG. 7) within the incubator bank module 16. Incubation chambers 18 function to maintain critical controlled conditions for health and long term culture of cells in culture vessels. Incubation tray(s) 20 may be mounted within incubation chamber 18, and incubation chamber 18 are mounted within incubator bank module 16. In an exemplary embodiment, up to three incubation chambers 18 each having a height of 6 inches are mounted in incubator bank module 16. Other exemplary incubation chambers 18 that are mounted in incubator bank module 16 include two incubation chambers 18 each chamber having a height of 10 inches or a single incubation chamber 18 having a height of 22 inches. It is within the scope of the present disclosure that more or fewer incubation chambers 18 with alternate heights may be mounted within incubator bank module 16. In an exemplary embodiment, the incubation chamber 18 includes a removable rack, slide out trays, and/or a water pan.

A controller 17 (FIG. 7) is coupled to incubation chamber(s) 18, and the controller 17 monitors and/or controls the selected variables (e.g., oxygen content) in one or more incubation chambers 18. The controller can function external from the chamber by remotely sensing (e.g., oxygen content sensors) and actuating cell variables (e.g., oxygen content) inside the chamber. It is within the scope of the present disclosure that the controller not only maintains hypoxic conditions within the processing chambers 14A-D, but also can vary the conditions among the chambers 14A-D. That is, a wide array of oxygen tensions can be obtained in the sealed system or other modifications to gas content could be altered (i.e., low or high oxygen contents in physiological or pathophysiological states, hypoxia, hyperoxia, study of effects of non-volatile gasses etc.). For example, one processing chamber may be maintained under 3% hypoxic conditions while another chamber may be maintained under 5% hypoxia, hyperoxic, ambient air conditions, etc. while yet another chamber may have a gas applied within the chamber.

In operation, each unit of sealed chamber 10 can be independently set to various oxygen tensions and can be modified at the experimenter's discretion. Other experimental parameters may also be modified (e.g., temperature).

A computer (generally indicated as 22), having the required software, is coupled to units (e.g., processing chambers 14A-D) of sealed chamber 10 and allows for consistent monitoring of desired and actual oxygen tension(s) for each processing chamber 14A-D as well as buffer chambers 12A-C. Other parameters may be monitored as well such as carbon dioxide (CO2) control, temperature control, hepafiltration etc. During cell sample processing (including centrifugation, staining and all experimental aspects), oxygen tension is controlled in a chamber designated for harvesting. The oxygen tension is also controlled in a chamber designated for sorting. The sheath fluid is in an adjacent chamber, and the oxygen tension of the fluid will be established/induced manually by the operator and subsequently maintained at the same oxygen tension level as the sorting chamber.

As discussed, sealed chamber 10 includes additional chambers for various functions (e.g., a test subject injection chamber, incubator chamber, and processing chamber with centrifuge) so that (1) a cell sorter device 60 (FIGS. 8 and 10) can be placed and be functional in sealed chamber 10, (2) the fluidics of sealed chamber 10 allow for maintenance of low oxygen conditions throughout cell sorting and cell isolation, and (3) the cells remain in the created environment (e.g., hypoxic or other) from harvest to sorting to the conclusion of the experiment. From a scientific standpoint the disclosed cell sorter configuration allows for the collection and examination of cell populations in a hypoxic, clean environment that were previously unable to be obtained. This is relevant since most tissues in the body naturally reside in a low oxygen content environment (1-9% oxygen) and IPS (Induced Pluripotent Stem Cells) and other cell therapies may be enhanced by providing optimal gas and/or oxygen tension(s) that mimics the environment from the start of the creation and subsequently allows for selection of cell populations of interest (from many origins including but not limited to hematopoietic, muscle, mesenchymal, bone, adipose derived, cardiac derived etc.) as well as other potential applications. To that end, cell sorting outside the chamber will not retain these cell populations under the specific conditions as exposure to environmental conditions that deviate from the experimental conditions can change cell phenotype since changes to cell phenotype and function occur in less than 10 minutes. All cell types which are typically found in a hypoxic, or specific $O_2$ environment, may not only perform better but be more physiologically and clinically relevant if they can be retained, sorted, expanded, analyzed, and utilized there using this technology.

Advantageously, sealed chamber 10 allows for the ability to process sorted cells through to transplant, or experimental stages (including addition of equipment into the sealed chamber as well as modification of assays, etc. to perform in this system), under desired low oxygen tension (or other oxygen tensions or experimental parameters (e.g., temperature) as desired by the experimenter) in a heapae-filtered environment without exposure to external environmental conditions that could alter cell phenotypes. The system has been made, and validated to ensure that considerations of sealed chamber 10 such as various inputs, work flow, air handling, particle/heat generation, fluidics, oxygen tension maintenance, experimental and analysis (in vitro and in vivo) capabilities and cell fidelity have been addressed.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:
1. A sealed chamber comprising:
a processing chamber sealed from the outside air including an extended glove front coupled to and extending from a front face of the processing chamber, the extended glove front comprising a door coupled to the front face and a pair of gloves extending inwardly into the processing chamber;

a buffer module adjacent to the processing chamber and having a side door to insert a test subject, an inner door to access the processing chamber, and an airlock system capable of modifying the air content within the buffer module; and an enclosed holder in the sealed chamber that is capable of holding the test subject and having a removable cap and a plunger configured to sequester the test subject in a part of the holder;

wherein the sealed chamber is a sealed system such that cells can be placed under consistent conditions such that cells can be sorted, obtained, and analyzed under consistent conditions.

2. The sealed chamber of claim 1, further comprising a second processing chamber that includes a door hingedly coupled to a front face of the second processing chamber, the door further including a single glove that extends inwardly into the second processing chamber.

3. The sealed chamber of claim 1, further including an incubator bank module adjacent to the processing chamber, wherein the incubator bank module is coupled to a controller.

4. The sealed chamber of claim 3, further comprising a second processing chamber, a third processing chamber, and a fourth processing chamber; and a second buffer module, and a third buffer module;

wherein the processing chamber is adjacent to the buffer module and second buffer module, the second processing chamber is adjacent to the second and third buffer modules, and the third processing chamber is adjacent to the third buffer module and the fourth processing chamber.

5. The sealed chamber of claim 4, wherein the incubator bank module is adjacent to the second processing chamber.

6. The sealed chamber of claim 1, wherein the extended glove front extends from the front face of the at least one processing chamber by between 0.25 inches to 2 inches.

7. The sealed chamber of claim 1, wherein the processing chamber further includes a plurality of apertures in a rear face of the processing chamber configured to receive cables of additional processing units, wherein the additional processing units function to maintain operating conditions of the sealed chamber.

8. The sealed chamber of claim 1, further comprising a cell sorter located within the processing chamber.

9. The sealed chamber of claim 1, wherein the sealed chamber is maintained under hypoxic conditions.

* * * * *